US006248335B1

(12) United States Patent
Duan et al.

(10) Patent No.: US 6,248,335 B1
(45) Date of Patent: *Jun. 19, 2001

(54) STABILIZED ORAL PHARMACEUTICAL COMPOSITION CONTAINING IODIDE AND IODATE AND METHOD

(75) Inventors: Yongjun Duan, Lexington; Kirk Dinehart, Holliston; John Hickey, Marlborough; Jack Kessler, Southborough, all of MA (US)

(73) Assignee: Symbollon Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/258,062

(22) Filed: Feb. 26, 1999

Related U.S. Application Data

(63) Continuation-in-part of application No. 08/960,149, filed on Oct. 29, 1997, now Pat. No. 5,885,592.

(51) Int. Cl.[7] .............................. A61K 9/00; A61K 33/36
(52) U.S. Cl. .......................... 424/400; 424/667; 424/668; 424/669; 424/670; 424/671
(58) Field of Search ..................... 424/667, 668, 424/669, 670, 671, 400, 464, 476–482

(56) References Cited

U.S. PATENT DOCUMENTS 5,885,592 * 3/1999 Duan et al. ......................... 424/400

OTHER PUBLICATIONS

Remy, "Treatise on Inorganic Chemistry," Elsevier, New York, 1956, p. 780–781, 812–813.*

* cited by examiner

Primary Examiner—Russell Travers
Assistant Examiner—Shengjun Wang
(74) Attorney, Agent, or Firm—Anderson, Kill & Olick P.C.

(57) ABSTRACT

A stabilized solid oral pharmaceutical composition comprised of iodide and iodate as the active agents in the presence of one or more pharmaceutical excipients and a method for preparing these stabilized compositions.

13 Claims, No Drawings

STABILIZED ORAL PHARMACEUTICAL COMPOSITION CONTAINING IODIDE AND IODATE AND METHOD

This application is a continuation in part of Ser. No. 08/960,149, filed Oct. 29, 1997, U.S. Pat. No. 5,885,592.

FIELD OF THE INVENTION

This invention describes a stabilize an oral pharmaceutical composition comprised of iodide and iodate as the active agents in the presence of other pharmaceutical excipients and method for preparing these stabilized compositions.

BACKGROUND OF THE INVENTION

U.S. application Ser. No. 08/960,149 filed on Oct. 29, 1997, the disclosure of which is herein incorporated by reference, describes a method of generating molecular iodine in the stomach of a human or animal using an iodine reductant and an iodine oxidant. One reductant/oxidant pair identified as one of the preferred embodiments in this invention is iodide and iodate. One reason that iodide and iodate are preferred is that both of these compounds are used separately as food additives and both have GRAS (generally regarded as safe) status in the U.S. The literature describes the stability of iodide and iodate individually but there are no published reports of the stability of these two compounds in combination. In fact, these two chemicals in an appropriate medium can react rapidly with each other to yield molecular iodine.

This invention describes methods and compositions to stabilize an oral pharmaceutical composition that generates molecular iodine in situ wherein the active agents in said compositions are iodide and iodate. Methods for preparation of said stabilized pharmaceutical compositions are also described. It is a further objective of this invention to set forth the conditions and materials necessary to formulate a stable dosage form of iodide and iodate in the presence of accepted pharmaceutical excipients. It is a further objective of this invention to identify methods and compositions that comply with the strict stability objectives embodied in published regulatory guidelines of the FDA.

Regulatory bodies in different territories around the world have published guidelines that define requirements that must be met to manufacture and distribute a new pharmaceutical agent for human and animal use. In the U.S. the Food and Drug Administration (FDA) regulates drugs. Stability testing is a mandated aspect of the FDA drug development process and is required for manufacture and distribution of drugs.

DETAILED DESCRIPTION OF THE INVENTION

For the purposes of this invention the term iodide is the iodide anion which is commonly represented as $I^-$. Iodide salts such as calcium iodide, sodium iodide, potassium iodide, magnesium iodide, zinc iodide, cupric iodide, and manganese iodide are readily available and are representative of the types of compounds that can, individually or in combination, serve as a suitable source of iodide. In fact, for the purpose of this application "a source of iodide" includes any nontoxic chemical entity that releases iodide anion upon dissolution in water.

For the purposes of this application the term iodate is the iodate anion which is commonly represented as $IO_3^-$. Iodate salts such as calcium iodate, sodium iodate, potassium iodate, magnesium iodate, zinc iodate, cupric iodate, and manganese iodate are easily obtained and are representative of the types of entities that can, individually or in combination, serve as a suitable source of iodate. In fact, for the purpose of this application "a source of iodate" includes any chemical entity that releases the iodate anion upon dissolution in water.

For the purposes of this invention the term "oral pharmaceutical composition of iodide and iodate" shall mean a composition comprised of pharmaceutically acceptable excipients combined with iodide and iodate. Such a composition is to be administered orally to an animal or human. Suitable excipients include sodium alginate, alginic acid, dicalcium phosphates, tricalcium phosphate, microcellulose, citric acid, fructose, magnesium stearate, α-cyclodextrin, β-cyclodextri, γ-cyclodextrin, povidone, hydroxypropylmethylcelluiose, hydroxypropylmethylcellulose phthalate, disodium phosphate, sodium stearate, sorbitol, starch, sucrose, sodium acetate, sodium carboxymethylcellulose, ethyl vanillin, mannitol, sodium chloride, calcium sulfate, maltodextrin, dextrose, dextrin, dextrates, myvatex-TL, and saccharin. Other pharmaceutically acceptable excipients known in the art may also be used. The iodide and iodate are preferably uniformly dispersed. For example, in the case of a solid this can be accomplished by means of a granulation or by "slugging" both iodide and iodate with selected excipients. Common solid pharmaceutical dosage formats such as tablets, capsules or powders are suitable for this invention as is a liquid solution.

For the purposes of this application the term "granulation solution pH" is the pH of the solution for granulation that contains at least one of the following two components: iodide and iodate. If such solution for granulation contains only one of the two active components (iodide/iodate) then the second active will be combined during the granulation onto the pharmaceutical excipients. Such solution for granulation is combined with suitable pharmaceutical excipients alone or in combination with either iodide or iodate to prepare a wet granulation of an oral pharmaceutical composition of iodide or iodate. It is highly preferred to combine both iodate and iodide in the granulation solution to insure a homogeneous composition.

For the purposes of this application the term "pH control agents" shall refer to chemicals that control the "effective pH" of the dried granulation. The effective pH is measured by preparing a 10% (w/v) solution of a granulation or tablet in distilled water and determining the pH. Suitable pH control agents include sodium carbonate, calcium carbonate, potassium carbonate, magnesium carbonate, sodium hydroxide, bentonite ($Al_2O_3.4SiO_2.H_2O$), dibasic calcium phosphate dihydrate, magnesium oxide, magnesium trisilicate, sodium bicarbonate, dibasic sodium phosphate, tribasic sodium phosphate, dibasic potassium phosphate, and tribasic potassium phosphate.

This invention describes methods and compositions that allow iodide and iodate to be combined to form an oral pharmaceutical composition of iodide and iodate with iodide and iodate stability adequate to meet regulatory requirements. Regulatory requirements mandate that 100±10% of the concentration of a drug be maintained while it is used in general commerce. However, maintaining at least 90% of the initial concentration of two reactive agents that are held in intimate contact with each other is difficult.

Example 1 demonstrates that it is possible to stabilize iodide and iodate on a pharmaceutical excipient. In this example, and every other observation thereafter, it is clear that it is necessary to carefully control the pH of the process of preparing these compositions if adequate stability is to be achieved. At an effective pH above 7.0, solid compositions of iodide and iodate exhibit stability that is adequate for a pharmaceutical product. Neither iodide nor iodate are materially effected by a pH even as high as 12.0.

Every example provided in this invention supports the need to control the pH of iodide and iodate to achieve the stability mandated in a regulated product. The inventors have identified a group of preferred pH control agents to accomplish this objective. These agents include sodium carbonate, calcium carbonate, potassium carbonate, magnesium carbonate, sodium hydroxide, bentonite ($Al_2O_3.4SiO_2.H_2O$), dibasic calcium phosphate dihydrate, magnesium oxide, magnesium trisilicate, sodium bicarbonate, dibasic sodium phosphate, tribasic sodium phosphate, dibasic potassium phosphate, tribasic potassium phosphate, dibasic potassium phosphate, and tribasic potassium phosphate. These agents can be used alone or in combination. The amount of one or more pH control agents necessary to provide a beneficial pH will depend upon the particular pH control agents, the manufacturing process, and the other pharmaceutical excipients. For instance, the amount of a pH control agent necessary to achieve a pH of 7.0 with any given excipient will vary. Our observations indicate that it takes considerably more pH control agent to bring a given amount of sorbitol to a pH of 7.0 than mannitol. In fact, the amount of a pH control agent necessary to achieve a specific pH, can vary with different lots of the same material from the same vendor.

A preferred method of preparation for a solid composition is to perform a granulation using a granulating solution that contains both iodide and iodate. In this instance the pH of the granulation solution should be controlled to a pH value that is greater than 7.0 and preferably greater than 8.0 using one of the pH control agents. The granulation solution can contain binding agents such as dextrose, sucrose, sorbitol, maltodextrin, dextrins, fructose, sucrose, hydroxypropylmethylcellulose, or other commonly used binding agents. Iodide and iodate should not be dissolved in the granulation solution until the pH control agent(s) has been dissolved to insure that the pH is greater than 7.0 and preferably greater than 8.0.

Once a solid granulation is prepared care must be taken to insure that the this solid is dried properly. The residual moisture content in the dried solid should be less than 2%. If the moisture content of the granulation is above 2% the stability of the active agents can be compromised. Once dried the granulation can be pressed into tablets, filled in capsules or administered as a powder.

The following examples should not be construed to be otherwise limiting.

EXAMPLES

Example 1—The stability of iodide/iodate solutions in the presence of a organic pharmaceutical excipient were evaluated at 40° C. as a function of pH. Aqueous solutions of sodium iodide (Deepwater Chemicals) and sodium iodate (Aldrich Chemical Company) were prepared in a 20% solution of sorbitol. The molar ratio of iodide to iodate in these solution was 5 to 1 respectively (3.80 grams of iodide for every 1.00 gram of iodate) the concentration of sodium iodide and sodium iodate was approximately 0.06 g/L and 0.1578 g/L respectively (w/v). The pH of these solutions was controlled by the addition of sodium hydroxide. The amount of sodium hydroxide added to achieve the desired pH values ranged from 0.02 to approximately 40 milligrams per gram of sorbitol.

Eight different 100 mL solutions were brought to the following pH values: 4.5, 6.0, 7.2, 8.3, 9.0, 10, 11.1 and 11.9. It was observed that immediately following preparation of the pH 4.5 sample the color in the sample turned from clear to yellow. The pH 6.0 sample began to turn yellow approximately 60 minutes after preparation. After preparation the samples were stored in sealed glass containers in a temperature controlled oven at 40° C.

The stability analysis was performed as follows. A 5.0 mL aliquot was removed from the 100 mL sample in the 40° C. oven and the 5.0 mL aliquot was transferred into 190 mL of water and the concentration of iodide was measured. Iodide levels was measured using an iodide selective electrode (ISE) from Corning of NY (Catalog No. 476127). Calibration of the iodide selective electrode was accomplished by using standards prepared from reagent grade sodium iodide and plotting the mV response from a pH meter (Corning Model 345) versus concentration. After the iodide-ISE measurement, the iodate concentration in a sample was determined by iodometric titration of oxidative capacity. This was accomplished by treating the sample to make it 0.1N with respect to hydrochloric acid and then sodium thiosulfate was used to measure the oxidative capacity (i.e., thiosulfate titratable iodine).

The results of the stability measurements for iodate are shown below in Table 1A below. The results of the stability measurements for iodide are shown below in Table 1B below.

TABLE 1A

Percent Initial Iodate Concentration at 40° C. in a 20% Sorbitol Solution vs pH

| Day | pH 4.3 | pH 6.0 | pH 7.2 | pH 8.3 | pH 9.0 | pH 10 | pH 11.1 | pH 11.9 |
|---|---|---|---|---|---|---|---|---|
| 0 | 100 | 100 | 100 | 100 | 100 | 100 | 100 | 100 |
| 11 | 61 | 61 | 64 | 85 | 96 | 101 | 98 | 97 |
| 24 | 27 | 25 | 28 | 49 | 62 | 98 | 97 | 96 |

TABLE 1B

Percent Initial Iodide Concentration at 40° C. in a 20% Sorbitol Solution vs pH

| Day | pH 4.3 | pH 6.0 | pH 7.2 | pH 8.3 | pH 9.0 | pH 10 | pH 11.1 | pH 11.9 |
|---|---|---|---|---|---|---|---|---|
| 0 | 100 | 100 | 100 | 100 | 100 | 100 | 100 | 100 |
| 11 | 89 | 96 | 94 | 102 | 101 | 103 | 100 | 103 |
| 24 | 87 | 89 | 97 | 97 | 94 | 98 | 99 | 103 |

The results obtained in Table 1A indicate that the stability of iodate is increased when the solution is maintained within a specific pH range. Iodide is also lost at the lower pH values. It is likely that some of the iodide is being converted into molecular iodine at pH values below 7.0.

Example 2—The experiment identified above as Example 1 was further explored using a series of well known and available pharmaceutical excipients. Saturated solutions of lactose, starch, fructose, dextrose, sucrose, mannitol, maltodextrin, and β-cyclodextrin were prepared at room temperature and filtered through glass wool. Water (800 mL) was added to 100 mL of the saturated excipient solutions. Aliquots (90 mL) were removed and brought to one of 5 different pH values (pH 7.0, 8.0, 9.0, 10.0 or 11.0) using tribasic sodium phosphate and sodium hydroxide. A defined concentration of sodium iodide and sodium iodate was added to each of the solutions after the pH was adjusted and the volume was adjusted to 100 mL with water. As used in Example 1, the molar ratio of iodide to iodate in these solutions was 5 to 1 respectively and the absolute concentration of sodium iodide and sodium iodate was 0.06 g/L and 0.1578 g/L respectively(w/v). The samples were stored at 40° C. in a temperature controlled oven.

Samples were analyzed for iodate using the method described above in Example 1. As can be seen in Table 2 below, the stability of iodate in the presence of these diverse excipients is comparable to that observed with sorbitol within a pH range of 7 to 11. This data suggests that the pH dependence of iodide/iodate mixtures with pharmaceutical excipients is a generated phenomenon Additionally, the most preferred pH range of these solutions with regard to stability was between 8 and 11.

TABLE 2

Percent of the Initial Iodate Concentration of 10% Saturated Solutions of Pharmaceutical Excipients Stored at 40° C.

| Conditions | pH 7.0 | pH 8.0 | pH 9.0 | pH 10 | pH 11 |
|---|---|---|---|---|---|
| Lactose - Day 12 | 38 | 65 | 82 | 96 | 94 |
| Lactose - Day 24 | 24 | 38 | 66 | 92 | 97 |
| Starch - Day 12 | 60 | 86 | 95 | 96 | 96 |
| Starch - Day 24 | 33 | 35 | 57 | 81 | 93 |
| Fructose - Day 12 | 42 | 63 | 83 | 98 | 96 |
| Fructose - Day 24 | 24 | 32 | 48 | 90 | 98 |
| Dextrose - Day 12 | 59 | 74 | 88 | 94 | 93 |
| Dextrose - Day 24 | 25 | 31 | 46 | 98 | 97 |
| Sucrose - Day 12 | 62 | 81 | 94 | 96 | 95 |
| Sucrose - Day 24 | 31 | 32 | 43 | 85 | 91 |
| Mannitol - Day 12 | 77 | 85 | 97 | 99 | 97 |
| Mannitol - Day 24 | 43 | 52 | 68 | 97 | 98 |
| Maltodextrin - Day 12 | 69 | 83 | 97 | 97 | 99 |
| Maltodextrin - Day 24 | 36 | 47 | 65 | 98 | 98 |
| β-Cyclodextrin - Day 12 | 73 | 88 | 97 | 98 | 99 |
| β-Cyclodextrin - Day 24 | 43 | 52 | 68 | 97 | 99 |

Example 3—Iodate/iodide were granulated in the presence of sorbitol under a variety of pH values. Coating solutions contained 10% sorbitol, 6 grams NaI per 100 mL and 1.578 grams NaIO$_3$ per 100 mL. The pH of the coating solutions were controlled by adding sodium hydroxide. The "effective pH" of a completely dried granulation was determined by measuring the pH of a 10% solution made from the dried granulation.

For each experiment, 500 grams of sorbitol was weighed into a KitchenAid food processor. The speed control on the KitchAid was set to #2 and 30 mL of a coating solution was added slowly in aliquots of 0.250 mL. The granulation was then stirred for an additional 20 to 30 minutes. The granulation solution was transferred to a vacuum oven and dried at 45° C. After at least 12 hours of drying in the vacuum oven, samples were allowed to cool to room temperature under vacuum. A sample of the dried granulation was then stored in a 20 mL glass scintillation vial (uncapped) and placed in a temperature controlled oven at 40° C. The stability of the resulting granulations at 40° C. was then measured periodically during the next 3 months.

The stability analysis was performed as follows. The scintillation vial was removed from the temperature controlled oven and allowed to cool to room temperature. After thermal equilibration of the sample, 1.0 gram was removed from the scintillation vial and dissolved in distilled water. The resulting solution was brought to a total volume of 50 mL and the concentration of iodide was measured as described in Example 1 using an ion selective electrode (ISE). After the iodide-ISE measurement, the iodate concentration in a sample was determined by ometric titration of oxidative capacity. The results of these measurements are shown in Table 3 below. The initial concentration of iodide on these granulations was approximately 3 mg iodide per gram of granulation. The initial concentration of iodate on these granulations was approximately 0.605 mg per gram of granulation.

tific 15AS-2). The drying time was varied to yield granulations that had moisture levels that varied from less to than 1% to approximately 12% (w/w). The drying condition for all sample preparations were 45° C. and the vacuum was about 28 inches of Hg. The moisture levels of these granulations were determined by loss on drying (Ohaus Moisture Balance 9713). The moisture content of these samples was varied from 0 to 7%. After preparation of the granulations, samples were stored in a temperature controlled oven at 40° C. in sealed glass scintillation vials. The concentration of iodide and iodate was analyzed as described above in Example 3. The results of these measurements for two separate experiments are shown below in Table 4.

TABLE 3

Percent Initial Iodide/Iodate Concentration for a Sorbitol Granulation Stored at 40° C. vs pH

| | pH 6.5 | | pH 7.43 | | pH 9.48 | | pH 10.1 | | pH 11.4 | |
|---|---|---|---|---|---|---|---|---|---|---|
| Weeks | $I^-$ | $IO_3^-$ | $I^-$ | $IO_3^-$ | $I^-$ | $IO_3^-$ | $I^-$ | $IO_3^-$ | $I^-$ | $IO_3^-$ |
| 0 | 100 | 100 | 100 | 100 | 100 | 100 | 100 | 100 | 100 | 100 |
| 1 | 92.2 | 92.3 | 95.0 | 99.5 | 93.6 | 100.8 | 96.9 | 99.3 | 100 | 100.7 |
| 2 | 80.0 | 84.1 | 104.0 | 100.0 | 105.3 | 98.3 | 98.5 | 100.3 | 99.0 | 99.4 |
| 4 | 78.4 | 80.9 | 101.3 | 99.8 | 102.4 | 99.3 | 98.6 | 100.7 | 101.8 | 99.8 |
| 12 | 76.5 | 78.3 | 104.0 | 101.9 | 98.3 | 99.8 | 101.2 | 101.7 | 100 | 100.1 |

TABLE 4

Iodide/Iodate Stability for a Sorbitol Granulation with an Effective pH of 7.5 Stored at 40° C. versus Water Content

| | Experiment A | | | | | | Experiment B | | | | | |
|---|---|---|---|---|---|---|---|---|---|---|---|---|
| | 7% Moisture | | 4% Moisture | | 0 ≤ 1% Moisture | | 12% Moisture | | 8% Moisture | | 2% Moisture | |
| Day | Iodide | Iodate | Iodide | Iodate | Iodide | Iodate | Iodide | Iodate | Iodide | Iodate | Iodide | Iodate |
| 0 | 100 | 100 | 100 | 100 | 100 | 100 | 100 | 100 | 100 | 100 | 100 | 100 |
| 11 | 88 | 92 | 80 | 93 | 97 | 101 | 84 | 95 | 90 | 96 | 94 | 99 |
| 17 | 89 | 88 | 76 | 88 | 98 | 102 | 83 | 92 | 82 | 92 | 98 | 101 |

At an effective pH of 6.5 there was a substantial loss of both iodide and iodate. These data suggest that the stability of an iodide/iodate granulation is a function of its effective pH.

Example 4—This example was designed to determine if the moisture content of a granulation influences the stability of either iodide or iodate. Several 500 gram granulations of sodium iodide and sodium iodate were prepared in a fashion similar to that described in Example 3 to yield an effective pH of 7.5. The amount of moisture in a granulation was controlled by varying the amount of time that these granulations resided in the vacuum oven (GCA/Precision Scien- The data indicate that moisture can adversely influence the stability of both iodide and iodate. At a moisture greater than 2% both iodide and iodate lost more than 10% of the initial iodide concentration. A similar observation was drawn with regard to iodate. The experiment suggests strongly that moisture can accelerate chemical instability under certain conditions.

Example 5—A series of granulations solutions were prepared at different pH values. Sodium iodide (444 grams), sodium iodate (117 grams), sorbitol (1,443.75 grams), were dissolved in 7.5 liters of water. After dissolution of the solids, one liter aliquots were removed and the pH of these aliquots were adjusted using sodium carbonate. The amount of sodium carbonate used varied from 2.5 to 70 grams.

Mannitol (3390 grams) and sodium carbonate (70 grams) were charged in a Hobart blender and mixed for 20 minutes. One liter of a granulation solution at a defined pH was gradually added to the mannitol/carbonate mixture over a period of 30 minutes. After the granulation solution was added, the mixture was stirred for an additional 10 minutes. The resulting granulation was dried in an oven (Blue M Electric Company, OVA-1048) at 45° C. for 3 days. The moisture content of the resulting granulation was less than 1% (Ohaus Moisture Balance, 9713). The dried granulation was sieved through a #20 sieve and then mixed in a V-blender (Patterson-Kelly Company, LR-7402) with talc (0.5% w/w; sieved through a #60 sieve) and crospovidone (5% w/w) for 5 minutes. The resulting mixture was compressed into oval tablets using 4 stations of a 16-station Stokes tablet press (F. J. Stokes Machine Company, 664534). Approximately 1,000 tablets with a weight of 400 mg (SD≈0.2%; n=20 ) were pressed with each of the different granulations.

The tablets were analyzed for their effective pH by dissolving 10 tablets into 75 mL of distilled water. After dissolution additional water was added to QS to 100 mL. The pH was measured under stirring with a Ciba-Corning 345 pH meter and a Corning pH probe (#476530). The stability of iodide and iodate was determined by placing the tablets in glass containers within a temperature controlled oven at a temperature of 50° C. For stability determination, individual tablets were removed from the oven and dissolved in an appropriate volume of distilled water for either an iodide or iodate analysis. Iodide was determined using an iodide ion selective electrode (see Example 1). Iodate was determined by titrating with sodium thiosulfate solution in the presence of a starch indicator until a light blue color disappeared (see Example 1).

Approximately three months of stability measurements on the tablets are shown in Table 5. The data suggest that the between-day precision of the iodate assay (titration) is superior to the iodide assay (ISE). Subsequent measurements confirm this observation. The data demonstrates two clear trends. The first trend was observed in the series of data corresponding to the pH 6.4 tablets; namely, iodate and iodide are unstable at this pH range. Visual observation of the tablets confirmed the formation color on the surfaces of the tablet. Presumably, this coloration corresponds to the formation of molecular iodine. The second trend was the uniform stability of the tablets that have an effective pH greater than 7.0.

TABLE 5

Iodide/Iodate Tablet Stability at 50° C. vs pH

% Initial Concentration of Iodide or Iodate

|  | Day 0 | Day 28 | Day 39 | Day 55 | Day 70 | Day 84 |
|---|---|---|---|---|---|---|
| pH 6.4 |  |  |  |  |  |  |
| Iodide | 100 | 93 | 96 | 91 | 86 | 83 |
| Iodate | 100 | 95 | 84 | 83 | 80 | 80 |
| pH 7.6 |  |  |  |  |  |  |
| Iodide | 100 | 99 | 98 | 102 | 99 | 97 |
| Iodate | 100 | 98 | 98 | 97 | 98 | 99 |
| pH 7.9 |  |  |  |  |  |  |
| Iodide | 100 | 98 | 104 | 100 | 95 | 98 |
| Iodate | 100 | 99 | 98 | 98 | 97 | 94 |

TABLE 5-continued

Iodide/Iodate Tablet Stability at 50° C. vs pH

% Initial Concentration of Iodide or Iodate

|  | Day 0 | Day 28 | Day 39 | Day 55 | Day 70 | Day 84 |
|---|---|---|---|---|---|---|
| pH 8.4 |  |  |  |  |  |  |
| Iodide | 100 | 99 | 98 | 102 | 99 | 97 |
| Iodate | 100 | 100 | 99 | 99 | 100 | 98 |
| pH 8.7 |  |  |  |  |  |  |
| Iodide | 100 | 95 | 98 | 94 | 101 | 102 |
| Iodate | 100 | 99 | 99 | 100 | 98 | 99 |
| pH 9.1 |  |  |  |  |  |  |
| Iodide | 100 | 96 | 98 | 98 | 103 | 97 |
| Iodate | 100 | 99 | 99 | 100 | 99 | 99 |
| pH 9.6 |  |  |  |  |  |  |
| Iodide | 100 | 99 | 101 | 102 | 98 | 94 |
| Iodate | 100 | 100 | 99 | 99 | 99 | 100 |
| pH 10.1 |  |  |  |  |  |  |
| Iodide | 100 | 96 | 99 | 97 | 98 | 101 |
| Iodate | 100 | 100 | 98 | 99 | 100 | 100 |

Example 6—A series of tablets were prepared to determine the effect, if any, of the agent used to control pH on the stability of iodide and iodate. For this purpose, sodium carbonate, calcium carbonate, potassium carbonate, magnesium carbonate, sodium hydroxide, bentonite ($Al_2O_3.4SiO_2.H_2O$), dibasic calcium phosphate dihydrate, cagnesium oxide, magnesium trisilicate, sodium bicarbonate, dibasic sodium phosphate and tribasic sodium phosphate were used individually in separate granulations to control the pH above 7.0.

The granulations were prepared as follows. Fructose (300 grams) and mannitol (100 grams) were mixed in a Kitchen Aid (KitchenAid-K45SS) for 5 minutes. The pH controlling agent was then added at a concentration that ranged from 2.5 and 10% w/w depending upon the agent used (see Table 6A below) and the powders were mixed for an additional 10 minutes.

The granulation solutions were prepared as follows. The following materials were dissolved in a 10% sucrose solution: 2.6% sodium iodate, 9.85% sodium iodide and a pH controlling agent at a concentration that range from 2 to 5% w/v (see Table 6A below). Some of the pH control agents were not completely soluble in water and in those instances suspensions were prepared and utilized. A Masterflex pump (#L91001556) was used to deliver 30 mLs of a granulation solution in 15 minute frame onto the granulation media that consisted of the fructose/sorbitol/pH-control agent mixture described above. The granulation was dried under vacuum at 45° C. (GCA Precision Scientific; 15AS-2) for 48 hours. A moisture determination using a moisture determination balance (Ohaus; #9713) was performed on all granulations after vacuum drying to insure that they contained less than 2% moisture.

The concentration of iodide and iodate was monitored every 4 weeks for 26 weeks. No loss of either iodide or iodate was observed. These observations suggest that stability is a function of pH and not a particular pH control agent.

What is claimed is:

1. A stabilized solid oral pharmaceutical composition comprising iodide and iodate in combination with at least one other pharmaceutical excipient including at least one pH control agent such that the effective pH of the composition is between 7.0 and 12.0.

2. A composition as defined in claim 1 wherein the source of iodide is selected from the group consisting of calcium iodide, sodium iodide, potassium iodide, magnesium iodide, zinc iodide, cupric iodide, and manganese iodide.

3. A composition as defined in claim 1 wherein the source of iodate is selected from the group consisting of calcium iodate, sodium iodate, potassium iodate, magnesium iodate, zinc iodate, cupric iodate, and manganese iodate.

4. A composition as defined in claim 1 wherein the pH control agent is selected from the class consisting of sodium carbonate, calcium carbonate, potassium carbonate, magnesium carbonate, sodium hydroxide, bentonite ($Al_2O_3.4SiO_2.H_2O$), dibasic calcium phosphate dihydrate, magnesium oxide, magnesium trisilicate, sodium bicarbonate, dibasic sodium phosphate, tribasic sodium phosphate, dibasic potassium phosphate, and tribasic potassium phosphate.

5. A composition as defined in claim 1 wherein the pharmaceutical excipients are selected from the class consisting of sodium alginate, alginic acid, dicalcium phosphate, tricalcium phosphate, microcellulose, citric acid, fructose, magnesium stearate, α-cyclodextrin, β-cyclodextrin, γ-cyclodextrin, povidone, hydroxypropylmethylcellulose, hydroxypropylmethylcellulose phthalate, disodium phosphate, sodium stearate, sorbitol, starch, sucrose, sodium acetate, sodium carboxymethylcellulose, ethyl vanillin, mannitol, sodium chloride, calcium sulfate, maltodextrin, dextrose, dextrin, dextrates, myvatex-TL, and saccharin.

6. A method for preparing a solid oral pharmaceutical composition with a moisture content of no more than about 2% containing iodide and iodate in combination with at least one pharmaceutically acceptable excipient including at least one pH control agent such that the effective pH of the composition is between 7.0 and 12.0, said methode comprises distributing iodate and iodide into a solid dosage form in a substantially homogeneous fashion and either (a) granulating a solution containing iodate and/or iodide onto pharmaceutically acceptable excipients or (b) slugging iodate and iodide into a solid matrix.

7. A method as defined in claim 6 where the source of iodide is selected from the group consisting of calcium iodide, sodium iodide, potassium iodide, magnesium iodide, zinc iodide, cupric iodide, and manganese iodide .

8. A method as defined in claim 6 where the source of iodate is selected from the group consisting of calcium iodate, sodium iodate, potassium iodate, magnesium iodate, zinc iodate, cupric iodate, and manganese iodate.

9. A method as defined in claim 6 where the pH control agent is selected from the group consisting of sodium carbonate, calcium carbonate, potassium carbonate, magnesium carbonate, sodium hydroxide, bentonite ($Al_2O_3.4SiO_2.H_2O$), dibasic calcium phosphate dihydrate, magnesium oxide, magnesium trisilicate, sodium bicarbonate, dibasic sodium phosphate, tribasic sodium phosphate, dibasic potassium phosphate, and tribasic potassium phosphate.

10. A method as defined in claim 6 where the pharmaceutical excipients are selected from the consisting of sodium algiate, alginic acid, dicalcium phosphate tricalcium group phosphate, microcellulose, citric acid, fructose, magnesium stearate, α-cyclodextrin, β-cyclodextrin, γ-cyclodextrin, povidone, hydroxypropylmethylcellulose, hydroxypropylmethylcellulose phthalate, disodium phosphates, sodium stearate, sorbitol, starch, sucrose, sodium acetate, sodium carboxymethylcellulose, ethyl vanillin, mannitol, sodium chloride, calcium sulfate, maltodextrin, dextrose, dextrin, dextrates, myvatex-TL, and saccharin.

11. A method as defined in claim 6 where the solid pharmaceutical composition is prepared by granulation of iodide and iodate onto pharmaceutical excipients and drying the composition.

12. A method as defined in claim 6 where iodide and iodate are dissolved into a granulation solution that has a pH greater than 7.0 and the granulation solution is then homogeneously coated onto pharmaceutical excipients.

13. A method as defined in claim 12, wherein the pH is greater than 8.0.

* * * * *